United States Patent [19]

Guthrie et al.

[11] 3,993,667

[45] Nov. 23, 1976

[54] HYDROXYCITRIC ACID DERIVATIVES

[75] Inventors: Robert William Guthrie, Fairfield; Richard Wightman Kierstead, North Caldwell, both of N.J.

[73] Assignee: Hoffmann-La Roche Inc., Nutley, N.J.

[22] Filed: Aug. 1, 1975

[21] Appl. No.: 600,996

Related U.S. Application Data

[62] Division of Ser. No. 376,478, July 5, 1973, Pat. No. 3,919,254, which is a division of Ser. No. 204,288, Dec. 2, 1971, Pat. No. 3,767,678.

[52] U.S. Cl. ............................................. 260/343.6
[51] Int. Cl.$^2$ ........................................ C07D 307/32
[58] Field of Search ................................ 260/343.6

[56] References Cited
UNITED STATES PATENTS 3,810,884  5/1974  Gold ................................ 260/343.6

*Primary Examiner*—Henry R. Jiles
*Assistant Examiner*—C. Jaisle
*Attorney, Agent, or Firm*—Samuel L. Welt; George M. Gould; Raymond R. Wittekind

[57] ABSTRACT

Ester and amide derivatives of three-hydroxycitric acid γ-lactone inhibit fatty acid synthesis in biological systems and are useful in the treatment of obesity and in correcting conditions of lipid abnormalities.

4 Claims, No Drawings

HYDROXYCITRIC ACID DERIVATIVES

This is a division of application Ser. No. 376,478, filed July 5, 1973, now U.S. Pat. No. 3,919,254, issued Nov. 11, 1975 which in turn is a division of application Ser. No. 204,288, filed Dec. 2, 1971, now U.S. Pat. No. 3,767,678, issued Oct. 23, 1973.

BRIEF DESCRIPTION OF THE INVENTION

The present invention relates to novel compounds of the formula

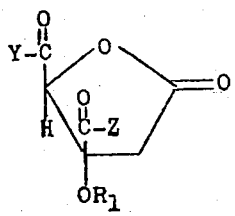

I wherein $R_1$ is hydrogen or lower alkanoyl; Y is one of the groups $CR_2'$ or $NR_3R_4$; Z is one of the groups $OR_2$ or $NR_5R_6$; where $R_2$ is hydrogen, lower alkyl, aryl lower alkyl or aryl; $R_2'$ is lower alkyl, aryl lower alkyl or aryl; $R_3$, $R_4$, $R_5$ and $R_6$ each taken independently is hydrogen, lower alkyl, cycloalkyl, aryl or aryl lower alkyl; $R_3$ and $R_4$ taken together with the adjacent nitrogen atom and $R_5$ and $R_6$ taken together with the adjacent nitrogen atom each independently form a 5- or 6-membered heterocyclic ring which may contain one additional heteroatom selected from the group consisting of nitrogen and oxygen;

and the optical antipodes and pharmaceutically acceptable salts thereof.

As used throughout the specification and the appended claims, the term "alkyl" shall mean a straight or branched chain hydrocarbon group containing no unsaturation and having up to 20 carbon atoms such as methyl, ethyl, hexyl, isopropyl, tert.-butyl, decyl, and so forth; the term "cycloalkyl" shall mean a saturated hydrocarbon group possessing at least one carbocyclic ring, said ring containing from 3 to 8 carbon atoms such as cyclopropyl, cyclopentyl, cyclohexyl, cyclooctyl, 1-adamantyl and so forth; the term "aryl" shall mean phenyl or phenyl monosubstituted with one of the following groups: halogen (i.e. chlorine, bromine, iodine or fluorine), lower alkyl, hydroxy, lower alkoxy, nitro, cyano, carboxyl or alkanoyl-amino. The term "alkanoyl" shall mean the residue formed by removing the hydroxyl portion from the carboxyl group of an alkanoic acid having up to 20 carbon atoms, such as formyl, acetyl, propionyl, pivaloyl, hexanoyl, and so forth. Examples of heterocyclic rings formed when $R_3$ and $R_4$ or $R_5$ and $R_6$ are taken together with the adjacent nitrogen atom are pyrrolidinyl, piperidinyl, morpholinyl and so forth. The term "lower" as applied to any of the foregoing groups denotes a group having a carbon skeleton containing up to and including 8 carbon atoms.

The compounds of formulas Ia and Ib are prepared by a novel sequence of reactions depicted in Reaction Scheme A. The starting material for this reaction sequence is racemic or optically active threo-hydroxycitric acid γ-lactone (II). The (+)-antipode of formula II is a well known natural product, Garcinia acid, obtainable by isolation from the fruit of Garcinia cambogia using known procedures.

It should be understood that the processes described herein may be employed either in the racemic or in the optically active series and that all of the novel compounds described herein may be prepared in the racemic or in either antipodal form. Where an optically active starting material of formula II is not utilized, suitable intermediates such as those of formula Ia can be resolved utilizing standard optical resolution techniques involving the separation of diastereomeric salts of the acid with an optically active base.

The novel compounds of the present invention may be conveniently prepared via the intermediate anhydride III. The anhydride is prepared from threohydroxy citric acid γ-lactone II by treatment of the latter with an anhydrating agent. An anhydrating agent is defined as an agent which serves to convert a cis-1,2-dicarboxylic acid to the corresponding anhydride. Suitable anhydrating agents include alkanoic acid anhydrides, for example acetic anhydride, propionic anhydride and so forth; and alkanoyl halides, for example acetyl chloride, propionyl chloride, and so forth.

REACTION SCHEME A

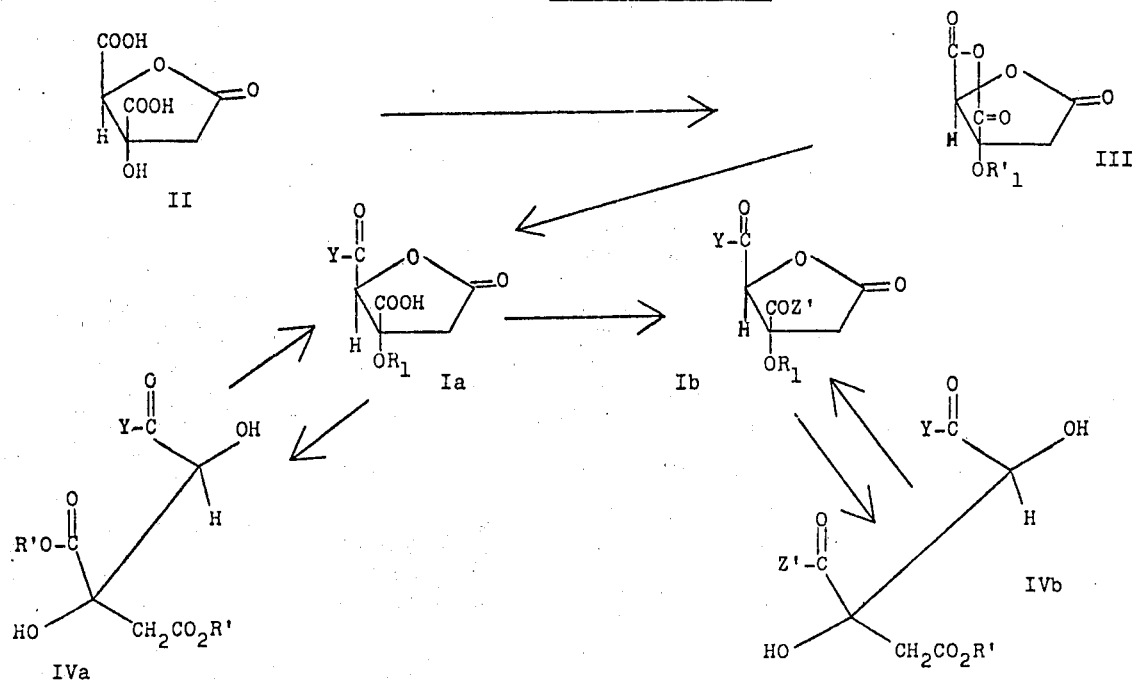

wherein $R_1$ and Y are as above, $R_1{'}$ is lower alkanoyl, $R'$ is lower alkyl, phenyl lower alkyl or aryl and $Z'$ is one of the groups $OR''_2$ or $NR_5R_6$, wherein $R''_2$ is lower alkyl, aryl lower lower alkyl or aryl and $R_5$ and $R_6$ are as above. The anhydrating agent effects both the conversion of the cis-dicarboxylic acid grouping to an anhydride and the conversion of the hydroxyl group to its lower alkanoly derivative. Thus, the alkanoyl portion of the anhydrating agent is retained as $R_1$ of the anhydride III.

The formation of the anhydride III may be conveniently carried out using an excess of the anhydration agent as the reaction medium, although an inert organic solvent may be employed as a diluent. Suitable inert organic solvents include hydrocarbons, e.g. benzene or toluene; organic ethers, e.g. dioxane or ethylene glycol dimethyl ether and so forth.

The anhydration reaction is suitably carried out at an elevated temperature in the range of from about 50° to about 150° C., most preferably from about 80° to about 120° C. In a particularly preferred procedure, a mixture of alkanoic acid anhydride and alkanoyl halide derived from the same alkanoic acid is employed as an anhydrating agent. The ratio of these reagents is not narrowly critical and a mole ratio of from about 1:9 to about 9:1 anhydride:halide is operable. A ratio of from about 1:2 to about 2:1 anhydride:halide is preferred.

The anhydride III is an excellent acylating agent for amines and alcohols. Thus, the anhydride III can be reacted either with an alcohol of the formula $R_2{'}OH$, where $R_2{'}$ is as above, with an amine of the formula $R_3R_4NH$, where $R_3$ and $R_4$ are as above, to afford, respectively, compounds of formula Ia-1 and Ia-2.

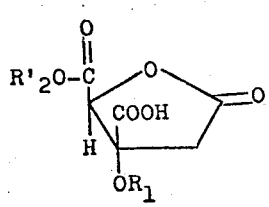

Ia-1

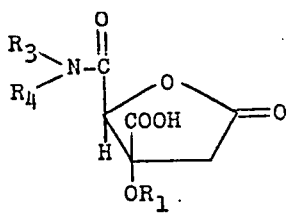

Ia-2 wherein $R_1$, $R_2{'}$, $R_3$ and $R_4$ are as above. The compounds prepared directly from the anhydride III are those members of the subgenuses Ia-1 and Ia-2 wherein $R_1$ is lower alkanoyl. The preparation of the remaining members of these subgenuses wherein $R_1$ is hydrogen is described below. This also applies for the preparation of compounds of formula Ib.

The reaction is suitably effected by treating the anhydride with an excess of either the amine or alcohol in an inert organic solvent. When an amine is used as a reactant, it is generally preferred to utilize at least 2 equivalents since one equivalent will react with the carboxyl group generated to form an addition salt. Suitable inert organic solvents include hydrocarbons, e.g. benzene, toluene, hexane and so forth; organic ethers, e.g. diethyl ether, tetrahydrofuran, dioxane and so forth; and the like. The acylation reaction may be carried out within a temperature range of from about −20° to about 150° C. A temperature range of from about 0° to 30° C. is preferred for amines and lower molecular weight alcohols. A temperature range of 75° to 100° C. is preferred for higher molecular weight alcohols.

The monosubstituted compounds of formula Ia can be converted to the disubstituted compounds of formula Ib in a two-step process comprising conversion of the free-carboxyl group to an active derivative such as an acyl halide, mixed anhydride or acyl imidazole, followed by reaction of this activated derivative with either an alcohol of the formula $R_2{''}OH$ or an amine of the formula $R_5R_6NH$. Compounds of formula Ia-1 are thus converted to compounds of formula Ib-1 and Ib-2, respectively.

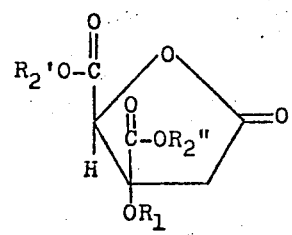

Ib-1

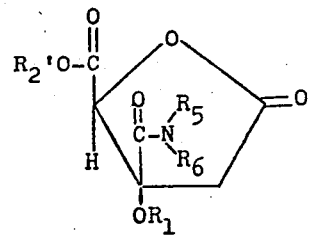

Ib-2 where $R_1$, $R_2{'}$, $R_2{''}$, $R_5$ and $R_6$ are as above. Compounds of formula Ia-2 are converted in this manner to compounds of formulas Ib-3 and Ib-4, respectively.

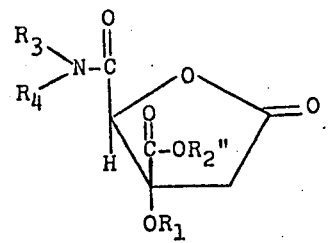

Ib-3

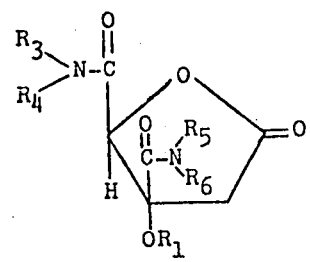

Ib-4 where $R_1$, $R_2{'}$, $R_2{''}$, $R_3$, $R_4$, $R_5$ and $R_6$ are as above.

Acyl halides of the carboxylic acids of formula Ia may be prepared by reacting the carboxylic acid with a suitable halogenating agent. Examples of suitable halogenating agents are, for example, thionyl chloride, oxalyl chloride, thionyl bromide, phosphorus trichloride, phosphorous tribromide and so forth. The acyl halides are prepared by reacting the carboxylic acid and halogenating agent in an inert organic solvent. Suitable inert organic solvents include hydrocarbons, e.g. benzene and toluene; organic ethers, e.g. diethyl ether, tetrahydrofuran and so forth. The halogenation reaction may be conveniently carried out at a temperature of from about 20° to about 150° C. A temperature of from about 50° to about 150° C. is preferred. The carboxylic acids of formula Ia can also be converted to other activated acyl derivatives such as acyl imidazoles. In this process, the carboxylic acid is treated with carbonyl diimidazole in an inert organic solvent at about room temperature.

The activated acyl derivatives described above are next reacted with the appropriate alcohol or amine to afford the compounds of formula Ib. This reaction may be carried out conveniently in an inert organic solvent such as hydrocarbons, e.g. benzene or toluene; organic ethers, e.g. diethyl ether, tetrahydrofuran or dioxane; organic esters, e.g. ethyl acetate; and the like. The reaction temperature may range from about 0° to about 100° C; although, a temperature of from about 0° to about room temperature is generally preferred.

Compounds of formula Ib-1 and Ib-3 wherein $R_2''$ is lower alkyl or aryl lower alkyl, may be prepared by reacting the carboxylic acid with the appropriate diazoalkylene or phenyl diazoalkylene, e.g. diazomethane, diazoethane or phenyl diazomethane in an inert organic solvent, preferably in an organic ether, at about room temperature.

In another aspect of the present invention, compounds Ia and Ib are converted to compounds of formulas IV-a and IV-b, respectively, by treatment with an alcohol, R'OH, where R' is as above, in the presence of a strong acid. In this reaction, alkanoylsis of the lactone ring, and concomitant esterification of the free carboxyl group as well as hydrolysis of the ester $OR_1$ occurs. The reaction is conveniently carried out in any suitable inert organic solvent, although, it is generally preferred to employ an excess of the alcohol reactant as the solvent. Suitable strong acids include mineral acid, e.g. hydrochloric acid, hydrobromic acid, sulfuric acid and so forth; organic sulfonic acids, e.g. p-toluene sulfonic acid and so forth; and the like. The strong acid may either be added directly to the reaction mixture or may be generated in situ by reaction of a suitable acid precursor with the alcohol present. Suitable acid precursors include the halogenating agents described above for the preparation of the acyl halides, such as thionyl chloride or oxalyl chloride. The alcoholysis reaction may be carried out at a temperature range of from about room temperature to about 100° C. It is particularly convenient to carry out the reaction at the boiling point of the reaction medium. Compounds of formulas IVa-1 and IVb-1.

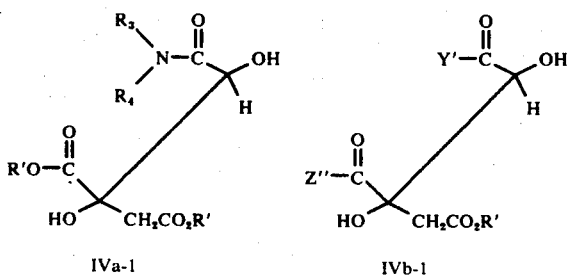

IVa-1    IVb-1 wherein R', $R_3$ and $R_4$ are as above, Y' is one of the groups $OR_2'$ or $NR_3R_4$, where $R_2$, $R_3$ and $R_4$ are as above, Z'' is one of the groups $OR_2''$ or $NR_5R_6$, wherein $R_2''$ is lower alkyl, aryl lower alkyl or aryl and $R_5$ and $R_6$ are as above, but with the added proviso that Y' cannot be $OR_2'$ when Z'' is $OR_2''$,
are novel and are useful in controlling lipogenesis.

Compounds of formulas Ia and Ib wherein $R_1$ is hydrogen may be prepared from compounds IVa and IVb, respectively, by lactonization. Suitable lactonization procedures include heating the compound of formula Ia or Ib with azeotropic removal of R'OH. A particularly preferred procedure is fractional distillation.

The compounds of formulas I and IV are useful for inhibiting fatty acid synthesis in biological systems. The biological systems in which the compounds of the present invention may be used include those containing citrate cleavage enzyme. Preferred biological systems are mammals, particularly non-ruminating mammals.

The inhibition of fatty acid synthesis in biological systems by the use of the compounds of the present invention is believed to arise from the inhibition by such compounds of citrate cleavage enzyme contained in such systems. The cleavage of citrate is catalyzed by citrate cleavage enzyme according to the stoichiometry: citrate + CoA + ATP → acetyl−CoA + oxaloacetate + ADP + $P_i$.

In the conversion of carbohydrates and various amino acids to fat by non-ruminating mammals, citrate is the major source of acetyl co-enzyme A, which is utilized for the synthesis of fatty acids. Citrate is formed in the mitochondria by the citrate synthase reaction. It is then metabolized via the citric acid cycle. Under conditions when energy intake exceeds energy demand, some citrate is diverted to the extra-mitochondrial space of the cell where it is used for fatty acid synthesis, that is to say, for energy storage. The novel compounds of formulas I and IV of the present invention are thus useful in the treatment of obesity and in the correction of lipid abnormalities.

As mentioned above, compounds of formula I may be used in the form of pharmaceutically acceptable salts. Preferred salts for this purpose include alkali metals, e.g. sodium or potassium the alkaline earth metals, e.g. calcium; or complex salts such as ammonium or substituted ammonium salts such as a mono-, di- or tri-alkylammonium salt or a mono-, di- or tri-hydroxyalkylammonium salt.

These compounds can be made up in the form of conventional pharmaceutical preparations; for example, the aforesaid compounds can be mixed with organic or inorganic inert pharmaceutical carriers suitable for parenteral or enteral administrations such as, for example, water, gelatin, lactose, starch, magnesium stearate, talc, vegetable oil, gums or the like. They can be administered in conventional pharmaceutical forms, e.g. solid forms, for example, tablets, capsules, dragees, suppositories, or the like; or in liquid forms, for example, solutions, suspensions, or emulsions. Moreover, the pharmaceutical compositions containing the compounds of this invention can be subjected to the conventional pharmaceutical expedients such as sterilization, and can contain conventional pharmaceutical excipients such as preservatives, stabilizing agents, emulsifying agents, salts for the adjustment of osmotic pressure or buffers. The compositions can also contain other therapeutically active materials.

A suitable pharmaceutical dosage unit can contain from about 15 to 600 mg. of the aforesaid compound.

Suitable parenteral dosage regimens in mammals comprise from about 1 mg/kg to about 25 mg/kg per day. However, for any particular subject, specific dosage regimens should be adjusted according to the individual need and the professional judgment of the person administering or supervising the administration of the aforesaid compounds. It is to be understood that the dosages set forth herein are exemplary only and that they do not, to any extent, limit the scope or practice of the invention.

The present invention may be more clearly illustrated by the following examples. All the temperatures are stated in degrees centigrade.

EXAMPLE 1

2(S),3(S)-Tetrahydro-3-acetoxy-5-oxo-furan-2,3-dicarboxylic acid anhydride

A. A mixture of (+)-threo-hydroxycitric acid γ lactone [2(S),3(S)-tetrahydro-3-hydroxy-5-oxo-furan-2,3-dicarboxylic acid, (+)-Garcinia acid] (28.0 g.) and acetic anhydride (150 ml.) was maintained at 95° (steam bath) for 30 minutes, then the solvent was removed under reduced pressure. A solution of the residue in methylene chloride was filtered to remove a small amount of insoluble material then was diluted with carbon tetrachloride. The resulting crystalline precipitate was collected by filtration to give 26.1 g. of the anhydride, mp 136°–139°. Recrystallization from methylene chloride-ether furnished the analytical sample, mp 142°–143°.

B. A solution of (+)-threo-hydroxycitric acid γ lactone (20 g.) in acetic anhydride (80 ml.) and acetyl chloride (40 ml.) was heated at reflux under anhydrous conditions for 90 minutes. The solvent was removed in vacuo to give 22 g. of the anhydride identical with that prepared in part A. above.

Anal. Calcd. for $C_8H_6O_7$: C, 44.87; H, 2.82; Found: C, 44.26; H, 2.98.

EXAMPLE 2

2(S),3(S)-Tetrahydro-2-methoxycarbonyl-3-acetoxy-5-oxo-3-furancarboxylic acid

The anhydride, prepared as in Example 1, (11.09 g.) was dissolved in anhydrous methanol (100 ml.) and heated to reflux for five minutes. The solvent was removed under reduced pressure and the resulting solid was dried under high vacuum. Crystallization from dry chloroform-carbon tetrachloride afforded 11.2 g. of the monoester, mp 116°–118°. The analytically pure sample was obtained from dry chloroform-hexane, mp 116°–118°; $[\alpha]_D^{25}$ +110.65° (c, 1.0, $CHCl_3$).

Anal. Calcd. for $C_9H_{10}O_8$: C, 43.91; H, 4.09; Found: C, 43.86; H, 4.28.

EXAMPLE 3

2(S),3(S)-Tetrahydro-2-ethoxycarbonyl-3-acetoxy-5-oxo-3-furancarboxylic acid

The anhydride, prepared as in Example 1, (6.5 g.) was dissolved in absolute ethanol (100 ml.) and heated to reflux for five minutes. The solvent was evaporated in vacuo to give 8.0 g. of a white solid. Crystallization from ether-hexane furnished 4.7 g. of the ethyl ester, m.p. 133°–135°. Concentration of the mother liquors gave an additional 2.0 g., mp 132°–134°. Recrystallization from ether-hexane afforded the pure material, mp 135°–136°; $[\alpha]_D^{25}$ +110.98°.

Anal. Calcd. for $C_{10}H_{13}O_7$: C, 46.16; H, 4.65; Found: C, 46.03; H, 4.57.

EXAMPLE 4

Methyl 2(S),3(S)-tetrahydro-3-acetoxy-3-carbamoyl-5-oxo-2-furancarboxylate

Oxalyl chloride (20 ml.) was added to a solution of the methyl ester, prepared as in Example 2, (6.2 g.) in dry tetrahydrofuran and the solution was refluxed for 30 minutes. The solution was evaporated in vacuo and residual oxalyl chloride was removed by repeated evaporation with dry benzene. The residual acid chloride was dissolved in dry tetrahydrofuran (50 ml.) and the solution was cooled to 0°. To this stirred solution, 25 ml. of a 2.3 M solution of ammonia in tetrahydrofuran was added rapidly. After one minute the solvent was removed under reduced pressure and the resulting oil was dissolved in water and extracted into ethyl acetate. The combined organic extracts were dried ($Na_2SO_4$) and concentrated to dryness to give 4.8 g. of crude amide as an oil. Crystallization from ethyl-hexane afforded 2.3 g. of the amide as a yellow solid, mp 161°–163°. Concentration of the mother liquors gave an additional 1.2 g. of material, mp 160°–163°. The combined crops were decolorized with charcoal and crystallized from ethyl acetate-hexane to give 2.8 g. of colorless crystals, mp 164°–166°. The analytically pure material was obtained from the same solvent system, mp 165°–166°, $[\alpha]_D^{25}$ + 129.42° (c, 1.0, MeOH).

Anal. Calcd. for $C_9H_{11}NO_7$: C, 44.09; H, 4.52; N, 5.71; Found: C, 44.03; H, 4.58; N, 5.49.

EXAMPLE 5

Ethyl 2(S),3(S)-tetrahydro-3-acetoxy-3-carbamoyl-5-oxo-2-furancarboxylate

A mixture of ethyl ester, prepared as in Example 3, (15 g.) and oxalyl chloride (60 ml.) was heated at reflux for 60 minutes then the solvent was removed in vacuo and the residual oxalyl chloride was eliminated through repeated evaporation with dry benzene. The crude acid chloride was dissolved in dry tetrahydrofuran and the solution was cooled in an ice-water bath then 80 ml. of a 2.3M solution of ammonia in tetrahydrofuran was added rapidly. The solution was evaporated immediately in vacuo at low temperature and the residue was dissolved in water and extracted with ethyl acetate. The organic extracts were dried ($Na_2SO_4$) and concentrated under reduced pressure to give 13 g. of crude amide as a yellow oil. Crystallization from ethyl acetatehexane furnished 9.8 g. of yellow crystals, mp 133°–135°. Decolorization using charcoal and subsequent recrystallization from ethyl acetate afforded analytically pure amide, mp 134°–5°, $[\alpha]_D^{25}$ + 108.84° (c, 1.0, $CHCl_3$).

Anal. Calcd. for $C_{10}H_{13}NO_7$: C, 46.34; H, 5.06; N, 5.40. Found: C, 46.12; H, 5.06; N, 5.24.

EXAMPLE 6

2(S),3(S)-Tetrahydro-2-(N-ethylcarbamoyl)-3-acetoxy-5-oxo-3-furancarboxylic acid A stirred solution of 78 mmol anhydride, prepared as in Example 1, in dry tetrahydrofuran (150 ml.) was treated with a solution of monoethylamine (8 g; 0.176 mol) in anhydrous tetrahydrofuran. The exothermic reaction was moderated by cooling in an ice-water bath. After five minutes the solvent was removed in vacuo and the residue was taken up in 1 N hydrochloric acid (180 ml.). The acidic mixture was extracted with ethyl acetate (2 ×) and the organic extracts were washed with brine. The combined ethyl acetate layers were dried ($Na_2SO_4$) and concentrated in vacuo to give 14.1 g. of a solid residue. Crystallization from ethyl acetate-carbon tetrachloride furnished 9.7 g. of the white crystalline amide, mp 161°–3°. The analytically pure material was obtained from the same solvent mixture, mp 161°–3°; $[\alpha]_D^{25}$ + 143.75° (c, 1.02, MeOH).

Anal. Calcd. for $C_{10}H_{13}NO_7$: C, 46.34; H, 5.06; N, 5.40; Found: C, 46.07; H, 5.24; N, 5.46.

EXAMPLE 7

2(S),3(S)-Tetrahydro-2-[N-(1-adamantylcarbamoyl)]-3-acetoxy-5-oxo-3-furancarboxylic acid To a stirred solution of anhydride, prepared as in Example 1, (9.8 g; 51.5 mmol) in dry tetrahydrofuran (250 ml.) was added a solution of 1-adamantanamine (16.8 g; 0.11 mol) in anhydrous tetrahydrofuran (100 ml.). After five minutes the solvent was removed in vacuo and the residue was dispersed in 1 N hydrochloric acid solution (150 ml.). The mixture was extracted with chloroform (3 ×) and the organic layers were washed in turn with 2% hydrochloric acid solution (1 ×) and with brine (2 ×). The combined extracts were dried ($MgSO_4$) and evaporated under pressure. The residue was crystallized twice from acetonehexane to give 17.7 g. of the amide, mp 129°–131° (dec). Recrystallization from acetone-hexane afforded the analytical sample as the acetone solvate, mp 130° (dec); $[\alpha]_D^{25}$ + 65.3° (c, 0.5, $CHCl_3$).

Anal. Calcd. for $C_{18}H_{23}NO_7 \cdot \frac{3}{4} C_3H_6O$: C, 59.52; H, 6.78; N, 3.43; Found: C, 59.71; H, 6.98; N, 3.33.

EXAMPLE 8

3(S), 2(S)-Tetrahydro-2-(N,N-diethylcarbamoyl)-3-acetoxy-5-oxo-3-furancarboxylic acid A solution of diethylamine (12.5 ml; 0.12 mol) in anhydrous tetrahydrofuran (100 ml.) was added rapidly to a stirred solution of 5.25 mmol of the anhydride, prepared as in Example 1, in dry tetrahydrofuran (100 ml.). The reaction was cooled throughout by means of an ice-water bath. After five minutes the reaction mixture was concentrated under reduced pressure and the resulting material was dissolved in 1 N hydrochloric acid solution (100 ml.). The acidic reaction mixture then was extracted with ethyl acetate (2 ×) and the organic layers were washed with 0.2 N hydrochloric acid. The combined extracts were dried ($MgSO_4$) and decolorized using charcoal and then were evaporated to dryness in vacuo. The residue was crystallized twice from methylene chloride-hexane to give 8.1 g. of pure diethylamide, mp 132°–3° (dec); $[\alpha]_D^{25}$ + 64.62° (c, 0.89, $CHCl_3$).

Anal. Calcd. for $C_{12}H_{17}NO_7$: C, 50.17; H, 5.96; N, 4.88; Found: C, 49.61; H, 5.95; N, 4.79.

EXAMPLE 9

Ethyl 3(S), 4(S)-4-[N-(1-adamantylcarbamoyl)]-3-ethoxycarbonyl-3,4-dihydroxybutanoate A solution of the amide acid, prepared as in Example 7, (1.0 g.) and oxalyl chloride (2 ml.) in absolute ethanol (30 ml.) was refluxed for one hour and then left at room temperature overnight. The reaction mixture was poured into sodium bicarbonate solution and extracted with ethyl acetate (2 ×). The organic layers were washed in turn with brine, dilute hydrochloric acid solution, dilute sodium bicarbonate solution and finally brine. The combined extracts were dried ($MgSO_4$) and concentrated to dryness under reduced pressure. Two crystallizations from ethyl acetate furnished 575 mg. of pure diol diester, mp 115°–6°. The analytically pure material was obtained from the same solvent mixture, mp 116°–7°; $[\alpha]$ −18.35° (c, 0.98, $CHCl_3$).

Anal. Calcd. for $C_{20}H_{31}NO_7$: C, 60.44; H, 7.89; N, 3.52; Found: C, 60.09; H, 7.76; N, 3.41.

EXAMPLE 10

Methyl 2(S), 3(S)-tetrahydro-2-(N,N-diethylcarbamoyl)-3-acetoxy-5-oxo-3-furancarboxylate A cooled solution of amide acid, prepared as in Example 8, (6.0 g.) in diethyl ether (125 ml.) was treated with a solution of diazomethane in ether until the yellow color persisted. The solution was left at room temperature until the excess diazomethane dissipated then the solvent was removed in vacuo. The resulting residue was crystallized twice from ether to yield 3.45 g. of the pure methyl ester, mp 103.5°–105°; $[\alpha]_D^{25}$ + 68.68° (c, 0.99, $CHCl_3$).

Anal. Calcd. for $C_{13}H_{19}NO_7$: C, 51.82; H, 6.36; N, 4.65; Found: C, 51.71; H, 6.41; N, 4.59.

EXAMPLE 11

Diethyl 2(S), 3(S)-tetrahydro-3-acetoxy-5-oxo-2,3-furan-dicarboxylate

A solution of the monoethyl ester, prepared as in Example 3, (1.0 g.) and oxalyl chloride (4 ml.) in tetrahydrofuran (20 ml.) was heated at reflux for thirty minutes then the solvent was removed under reduced pressure. The acid chloride was dissolved in 10 ml. of absolute ethanol and after several minutes the solvent was again removed in vacuo. The crude diester was dissolved in ethyl acetate and the solution was washed with aqueous sodium bicarbonate and with brine. The dried ($MgSO_4$) organic layer was concentrated to dryness in vacuo to give 530 mg. of the diester as an oil. This material was decolorized (charcoal) and crystallized (3 ×) from chilled ether-hexane solutions to give 230 mg. of the analytically pure diethyl ester, mp 39°–40°, $[\alpha]_D^{25}$ + 97.5° (c, 1.04, $CHCl_3$).

Anal. Calcd. for $C_{12}H_{16}O_8$: C, 50.00; H, 5.59; Found: C, 50.09; H, 5.61.

EXAMPLE 12

Ethyl 2(S), 3(S)-tetrahydro-3-(N-ethylcarbamoyl)-3-acetoxy-5-oxo-2-furancarboxylate A solution of the monoester, prepared as in Example 3, (1.0 g; 3.9 mmol) in dry tetrahydrofuran (20 ml.) containing oxalyl chloride (4 ml.) was refluxed for thirty minutes then was evaporated to dryness under reduced pressure. The residue was dissolved in dry tetrahydrofuran (20 ml.) and cooled to 0°–5° by means of a ice-water bath. To the stirred solution monoethylamine (346 mg; 7.8 mmol) in tetrahydrofuran (5 ml.) was added in one portion. After five minutes the reaction mixture was diluted with water and extracted with ethyl acetate (3 ×). The ethyl acetate extracts were washed in turn with sodium bicarbonate solution (2 ×) and brine (3 ×), then were combined, dried (MgSO$_4$) and evaporated in vacuo to give 0.9 g. of product. Crystallization of the crude material from chloroform-hexane afforded 720 mg. of the ethylamide, mp 131°–2°. Recrystallization from ethyl acetate-carbon tetrachloride furnished the analytically pure material, mp 134°–5°; [α]$_D^{25}$ + 101.26° (c, 1.035, CHCl$_3$).

Anal. Calcd. for C$_{12}$H$_{17}$NO$_7$: C, 50.17; H, 5.96; N, 4.88; Found: C, 50.20; H, 6.10; N, 4.84.

EXAMPLE 13

Ethyl 2(S), 3(S)-tetrahydro-3-(N,N-diethylcarbamoyl)-3-acetoxy-5-oxo-2-furancarboxylate A solution of the monoester, prepared as in Example 3, (10 g; 39 mmol) in tetrahydrofuran (100 ml.) contaning oxalyl chloride (40 ml.) was heated at reflux temperature for thirty minutes then the solvent was removed in vacuo. The crude acid chloride was dissolved in tetrahydrofuran (100 ml.) and to the cooled solution (0°–5°) diethylamine (10 ml; 96 mmol) was added. After five minutes the reaction mixture was diluted with water and extracted with ethyl acetate (3 ×). The organic extracts were washed with sodium bicarbonate solution (3 ×) and with brine (3 ×) then were combined, dried (MgSO$_4$) and evaporated. The residue was crystallized from ether to give 5.3 g. of the diethylamide, mp 81°–82°. The analytically pure material was obtained from the same solvent, mp 81°–82°; [α]$_D^{25}$ + 136.79° (c, 0.935, CHCl$_3$).

Anal. Calcd. for C$_{14}$H$_{21}$NO$_7$: C, 53.33; H, 6.71; N, 4.44; Found: C, 53.47; H, 6.78; N, 4.41.

EXAMPLE 14

Ethyl 2(S), 3(S)-tetrahydro-3-[N-(4-carboxyphenyl)carbamoyl]-3-acetoxy-5-oxo-2-furancarboxylate A solution of the monoester, prepared as in Example 3, (7.0 g; 27 mmol) and oxalyl chloride (28 mol) in tetrahydrofuran (140 ml.) were heated at reflux for thirty minutes. The solvent was evaporated to dryness in vacuo and the residual oxalyl chloride was removed by the repeated addition and evaporation of dry benzene. The crude acid chloride was dissolved in dry tetrahydrofuran (50 ml.) and to this stirred solution a solution of p-aminobenzoic acid (4.4 g; 32 mmol) and sodium hydroxide (1.32 g; 33 mol) in water (12 ml.) was added in one portion. After five minutes most of the solvent was removed under reduced pressure and the reaction mixture was diluted with ethyl acetate and washed with dilute hydrochloric acid (2 ×) and brine (2 ×). The organic layers were dried (MgSO$_4$) and concentrated to dryness in vacuo. The residue was dispersed in 1 N hydrochloric acid and extracted with chloroform (6 ×). The chloroform extracts were washed with water, then combined, dried (MgSO$_4$) and evaporated under reduced pressure. Crystallization of the residue from ethyl acetate-carbon tetrachloride furnished in two crops 5.0 g. of product, mp 187°, (dec). The analytically pure sample was obtained from ethylacetate-hexane, mp 187° (dec); [α]$_D^{25}$ + 139.8° (c, 0.9, MeOH).

Anal. Calcd. for C$_{17}$H$_{17}$NO$_9$: C, 53.83; H, 4.52; N, 3.69; Found: C, 53.69; H, 4.65; N, 3.69.

EXAMPLE 15

2(S), 3(S)-Tetrahydro-2-benzyloxycarbonyl-3-acetoxy-5-oxo-3-furancarboxylic acid To a solution of 15.8 mmol of the anhydride, prepared as in Example 1, in tetrahydrofuran (75 ml.) was added benzyl alcohol, (1.8 ml; 17.4 mmol) followed by pyridine (1.5 ml; 18.6 mmol). The solution was left at room temperature for two hours then most of the solvent was removed in vacuo. The residue was dissolved in water and washed with ether (2 ×). The aqueous layer was acidified with 1 N hydrochloric acid solution (20 ml.) and extracted with chloroform. Evaporation of the dried (Na$_2$SO$_4$) chloroform extracts furnished an oil. Crystallization from methanol-water afforded 3.5 g. of product as its monomethanol solvate, mp 79°–81.5°, [α]$_D^{25}$ + 93.7° (c, 0.5, MeOH).

Anal. Calcd. for C$_{15}$H$_{14}$O$_8$·CH$_3$OH: C, 54.24; H, 5.12; Found: C, 54.48; H, 5.21.

EXAMPLE 16

Diethylammonium 2(S), 3(S)-tetrahydro-2-benzyloxycarbonyl-3-acetoxy-5-oxo-3-furancarboxylate Diethylamine (1.65 ml; 16 mmol) was added to a solution of crude benzyl ester, prepared as in Example 15, (4.0 g; 12.5 mmol) and a white crystalline material began to form immediately. The solid was collected by filtration and washed with ether to give 4.0 g. of salt. Recrystallization from methanol-ether furnished 3.4 g. of the diethylammonium derivative, mp 128°–130°; [α]$_D^{25}$ + 101.81° (c, 0.94, CH$_3$OH).

Anal. Calcd. for C$_{19}$H$_{25}$NO$_8$: C, 57.71; H, 6.37; N, 3.54; Found: C, 58.17; H, 6.41; N, 3.49.

The pharmaceutical formulations in Examples 17 – 22 are illustrated for 2(S), 3(S)-tetrahydro-2-methoxycarbonyl-3-acetoxy-5-oxo-3-furancarboxylic acid. They are applicable to all the compounds of formulas I and IV.

EXAMPLE 17

| Capsule Formulation | Per Capsule |
| --- | --- |
| 2(S),3(S)-tetrahydro-2-methoxycarbonyl-3-acetoxy-5-oxo-3-furancarboxylic acid | 250 mg. |
| Lactose | 60 mg. |
| Corn Starch | 35 mg. |
| Magnesium Stearate | 5 mg. |
| Total Weight | 350 mg. |

PROCEDURE:

1) All of the ingredients were mixed until thoroughly blended in a suitable size container.

2) The powder was filled into 2, two piece, hard shell gelatin capsules to an approximate fill weight of 350 mg. using a Parke Davis capsulating machine. (Any similar type machine may be used.)

EXAMPLE 18

| Tablet Formulation | Per Tablet |
| --- | --- |
| 2(S),3(S)-tetrahydro-2-methoxycarbonyl-3-acetoxy-5-oxo-3-furancarboxylic acid | 200 mg. |
| Dicalcium Phosphate Dihydrate, Unmilled | 235 mg. |
| Corn Starch | 70 mg. |
| FD & C Yellow No. 5 - Aluminum Lake 25% | 2 mg. |
| Durkee 117 | 25 mg. |
| Calcium Stearate | 3 mg. |
| Total Weight | 535 mg. |

PROCEDURE:

1) All the ingredients were mixed thoroughly and Fitzed (Model D) using a 1A screen, medium speed.

2) The mixture was remixed and slugged.

3) The slugs were screened on an Oscillator through a 14 mesh screen and compressed on an "E" machine.

EXAMPLE 19

| Capsule Formulation | Per Capsule |
| --- | --- |
| 2(S),3(S)-tetrahydro-2-methoxycarbonyl-3-acetoxy-5-oxo-3-furancarboxylic acid | 50 mg. |
| Lactose, USP | 125 mg. |
| Corn Starch, USP | 30 mg. |
| Talc, USP | 5 mg. |
| Total Weight | 210 mg. |

PROCEDURE:

1) 2(S), 3(S)-Tetrahydro-2-methoxycarbonyl-3-acetoxy-5-oxo-3-furancarboxylic acid was mixed with lactose and corn starch in a suitable mixer.

2) The mixture was further blended by passing through a Fitzpatrick Comminuting Machine with a 1A screen with knives forward.

3) The blended powder was returned to the mixer, the talc added and blended thoroughly.

4) The mixture was filled into 4 hard shell gelatin capsules on a Parke Davis capsulating machine.

EXAMPLE 20

| Tablet Formulation | Per Tablet |
| --- | --- |
| 2(S),3(S)-tetrahydro-2-methoxycarbonyl-3-acetoxy-5-oxo-3-furancarboxylic acid | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

PROCEDURE:

1) 2(S), 3(S)-Tetrahydro-2-methoxycarbonyl-3-acetoxy-5-oxo-3-furancarboxylic acid and corn starch were mixed together and passed through a 00 screen in Model "J" Fitzmill with hammers forward.

2) This premix was then mixed with dicalcium phosphate and one-half of the magnesium stearate, passed through a 1A screen in Model "J" Fitzmill with knives forward, and slugged.

3) The slugs were passed through a 2A plate in a Model "D" Fitzmill at slow speed with knives forward, and the remaining magnesium stearate was added.

4) The mixture was mixed and compressed.

EXAMPLE 21

| Tablet Formulation | Per Tablet |
| --- | --- |
| 2(S),3(S)-tetrahydro-2-methoxycarbonyl-3-acetoxy-5-oxo-3-furancarboxylic acid | 100 mg. |
| Lactose, USP | 202 mg. |
| Corn Starch, USP | 80 mg. |
| Amijel B011* | 20 mg. |
| Calcium Stearate | 8 mg. |
| Total Weight | 410 mg. |

*A prehydrolyzed food grade corn starch. Any similar prehydrolyzed corn starch may be used.

PROCEDURE:

1) 2(S), 3(S)-Tetrahydro-2-methoxycarbonyl-3-acetoxy-5-oxo-3-furancarboxylic acid, lactose, corn starch, and Amijel B011 were blended in a suitable mixer.

2) The mixture was granulated to a heavy paste with water and the moist mass was passed through a 12 screen. It was then dried overnight at 110° F.

3) The dried granules were passed through a 16 screen and transferred to a suitable mixer. The calcium stearate was added and mixed until uniform.

4) The mixture was compressed at a tablet weight of 410 mg. using tablet punches having a diameter of approximately 3/8". (Tablets may be either flat or biconvex and may be scored if desired).

EXAMPLE 22

| Tablet Formulation | Per Tablet |
| --- | --- |
| 2(S),3(S)-tetrahydro-2-methoxycarbonyl-3-acetoxy-5-oxo-3-furancarboxylic acid | 500 mg. |
| Corn Starch | 30 mg. |
| Lactose | 88 mg. |
| Gelatin | 12 mg. |
| Talcum | 15 mg. |
| Magnesium Stearate | 5 mg. |
| Total Weight | 650 mg. |

PROCEDURE:

1) 2(S), 3(S)-Tetrahydro-2-methoxycarbonyl-3-acetoxy-5-oxo-3-furancarboxylic acid and lactose were thoroughly mixed in suitable blending equipment and granulated with a 10% gelatin solution.

2) The moist mass was passed through a 12 screen, and the granules were dried on paper lined trays overnight.

3) The dried granules were passed through a 14 screen and placed in a suitable mixer. The talcum and magnesium stearate were added and blended.

4) The granulation was compressed into tablets weighing approximately 650 mg. each, using punches having an approximate diameter of 12.7 mm. (½"). The final tablet thickness was about 5.1 mm.

EXAMPLE 23

Measurement of lipogenesis in vivo

Female Charles River rats weighing from 120–150 g. were provided free access to water and were fed a commercial diet prior to the initiation of the experiment. Each experimental group of animals were prefasted two days and then meal-fed a single meal daily from 9-12 a.m. The meal consisted of a 70% glucose fat-free diet (G-70) containing -70% glucose, 24% vitaminfree casein, 5% salt and 1% vitamins, to which 40 g. cellulose was added per kilogram.

On the last of feeding, at a specified time before initiation of the meal, the hydroxycitric acid derivative in ASV of the composition sodium chloride 0.9%, carboxy methyl cellulose 0.5%, benzyl alcohol 0.86% and tween 80 (polyoxyethylene sorbitan monoleate) 0.39% was administered. At a specified time after feeding, rats were lightly anaesthetized with Penthrane (methoxyflurane) and injected in the tail vein with 0.25 ml. of a solution with the following composition: 12.3 mg. alanine, $5\mu C^{14}$C-alanine (specific activity = 156 mC/mmole) as fatty acid precursor and 30.6 mg. a α-ketoglutarate as a transaminase acceptor dissolved in saline pH 7.4 – 7.6. After 30 minutes, rats were sacrificed by decapitation and their livers were excised, rapidly weighed, minced in 15 ml. water and homogenized in a Potter-Elvehjem homogenizer with 5 strokes of a drill press-driven teflon pestle. Duplicate 3-ml. aliquots of whole liver homogenates were added to tubes containing 2.1 ml. 5N NaOH and saponified with 2.6 ml. 5N $H_2SO_4$ and extracted twice with 5 ml. of petroleum ether (bp 40°–60°C.). Supernatants were added directly to glass counting vials, evaporated to dryness and 10 ml. of toluene-PPO-POPOP scintillation fluid was added. Samples were analyzed for absolute activity in a Packard Tri-carb scintillation counter. Resulting data was expressed as nanomoles $^{14}$C-alanine incorporated/gram of tissue/30 minutes.

Effect of oral administration of hydroxycitric acid derivatives (2.63 mmoles/kg) on in vivo rates of lipogenesis[1]

| Formula I Derivative (2S,3S-configuration, unless otherwise indicated)[2] | | | Lipogenesis | |
|---|---|---|---|---|
| Y | $R_1$ | Z | nanomoles $^{14}$C-alanine g. liver/30 min. | Percent Inhibition |
|  | ASV |  | 1022.4 ± 58.7(21)[3] | 0 |
|  | Saline |  | 1027.3 ± 47.9(9) | 0 |
| $CH_3O$ | $CH_3CO$ | $NH_2$ | 342.2 ± 133.6(4) | 67 |
| $C_2H_5O$ | $CH_3CO$ | $NH_2$ | 683.1 ± 124.0(8) | 33 |
| $C_2H_5NH_2$ | $CH_3CO$ | OH | 648.6 ± 104.9(7) | 37 |
| $(C_2H_5)_2N$ | $CH_3CO$ | OH | 858.8 ± 108.7(8) | 16 |
| $(C_2H_5)_2N$ | $CH_3CO$ | $CH_3O$ | 684.9 ± 114.5(8) | 33 |
| $C_2H_5O$ | $CH_3CO$ | $C_2H_5O$ | 616.8 ± 70.9(7) | 40 |
| $C_2H_5O$ | $CH_3CO$ | $C_2H_5NH$ | 452.6 ± 128.2(5) | 56 |
| $C_2H_5O$ | $CH_3CO$ | $(C_2H_5)_2N$ | 446.7 ± 42.5(6) | 56 |
| $C_2H_5O$ | $CH_3CO$ | p-HOOC—$C_6H_4$—NH | 838.0 ± 228.5(4) | 18 |
| $C_6H_5$—$CH_2$ | $CH_3CO$ | OH | 612.6 ± 96.1(5) | 40 |
| 1-adamantyl | $CH_3CO$ | OH | 476.6 ± 63.5(7) | 53 |
| Formula IV - Ethyl 3(S),4(S)-4-[N-(1-adamantylcarbamoyl)]-3-ethoxycarbonyl-3,4-dihydroxy-butanoate | | | 566.1 ± 59.0(7) | 45 |

[1]Rats were prefasted 2 days and meal-fed the G-70 diet, for 7–13 days. They were given the derivatives (2.63 mmoles/kg) by stomach tube 60 minutes prior to feeding on the experimental day, and assayed in vivo immediately after the meal.
[2]Derivatives were dissolved in ASV.
[3]Mean ± SEM for the number of rats indicated in parentheses.

We claim:
1. A compound of the formula

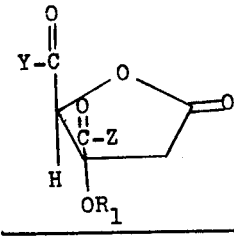

wherein $R_1$ is lower alkanoyl; Y is $OR_2'$; Z is $OR_2$; where $R_2$ is lower alkyl; $R_2'$ is lower alkyl; and the optical antipodes and pharmaceutically acceptable salts thereof.

2. The optical antipode of the compound of claim 1 having the 2(S), 3(S)-absolute configuration.

3. The compound of claim 1 wherein $R_1$ is acetyl.

4. The compound of claim 1 which is diethyl-tetrahydro-3-acetoxy-5-oxo-2,3-furan-dicarboxylate.

* * * * *